United States Patent [19]

Kawai et al.

[11] Patent Number: 4,824,945
[45] Date of Patent: Apr. 25, 1989

[54] HYPOCHOLESTEROLEMICALLY ACTIVE RNA FRACTIONS

[75] Inventors: Yasuo Kawai, Atsugi; Yoshiaki Oshida, Sagamihara, both of Japan

[73] Assignee: Kabushiki Kaisya Advance Kaithatsu Kenkyujo, Nihonba, Japan

[21] Appl. No.: 812,340

[22] Filed: Dec. 23, 1985

[30] Foreign Application Priority Data

Dec. 24, 1984 [JP] Japan .................. 59-270982

[51] Int. Cl.$^4$ ............... C07H 15/12; C12P 19/34; C12R 1/46; A61K 31/715
[52] U.S. Cl. ................... 536/27; 435/91; 435/885; 514/44
[58] Field of Search ............. 435/253, 885, 205, 91; 424/93, 94; 536/28, 29; 514/44

[56] References Cited

U.S. PATENT DOCUMENTS

| | | | |
|---|---|---|---|
| 3,567,821 | 3/1971 | Nouvel | 424/93 |
| 4,190,649 | 2/1980 | Beljanski | 424/180 |
| 4,259,442 | 3/1981 | Gayral | 435/36 |
| 4,297,272 | 10/1981 | D'Hinterland et al. | 530/395 |
| 4,335,239 | 6/1982 | Beljanski | 536/27 |
| 4,356,496 | 8/1985 | Shimizu et al. | 514/54 |
| 4,357,323 | 11/1982 | Soma et al. | 424/180 |
| 4,389,396 | 6/1983 | d'Hinterland et al. | 424/92 |
| 4,448,768 | 5/1984 | Coleman et al. | 424/92 |
| 4,579,733 | 4/1986 | Kawai et al. | 424/93 |
| 4,621,055 | 11/1986 | Theurer | 435/69 |
| 4,687,764 | 8/1987 | Kawai et al. | 514/54 |

FOREIGN PATENT DOCUMENTS

| | | | |
|---|---|---|---|
| 0013851 | 8/1980 | European Pat. Off. | 530/395 |
| 0029893 | 6/1981 | European Pat. Off. | 435/69 |
| 0101209 | 2/1984 | European Pat. Off. | 435/253 |
| EPA-101209 | 2/1984 | European Pat. Off. | 424/93 |
| 0115157 | 8/1984 | European Pat. Off. | 530/350 |
| EPA-115157 | 8/1984 | European Pat. Off. | 435/68 |
| 0186482 | 7/1986 | European Pat. Off. | 514/44 |
| 2106154 | 8/1972 | Fed. Rep. of Germany | 424/93 |
| 49-15280 | 4/1974 | Japan | 536/29 |
| 54-3100 | 1/1979 | Japan | 514/44 |
| 0122723 | 9/1980 | Japan | 424/93 |
| 58-131917 | 8/1983 | Japan | 424/93 |
| 930107 | 7/1963 | United Kingdom | 424/93 |
| 2090846 | 7/1982 | United Kingdom | 536/123 |

OTHER PUBLICATIONS

Chemical Abstracts, vol. 83, No. 1, 7th Jul. 1975, p. 606, Abstract No. 6996q, Columbus, Ohio, U.S.; B. Bueltmann et al., "Adjuvancy of *Streptococcal nucleic* Acids", and Z. Immunitaetsforsch. Exp. Klin. Immuno. 1975, 148(5), 425–430.

Nord et al., "Formation of Glycoside–Hydrolases by Oral Streptococci", Archs. Oral Biol., vol. 18, pp. 391–402 (1973).

Moore et al., "Cell–Free Protein Synthesis: Effects of Age and State of Ribosonal Aggregation", Science, vol. 154, pp. 1350–1353 (1966).

Herson et al., "Protein Synthesis in Cell–Free Extracts of *Streptococcus faecalis*", J. of Bacteriology, vol. 100, No. 3.

(List continued on next page.)

*Primary Examiner*—Elizabeth C. Weimar
*Attorney, Agent, or Firm*—Finnegan, Henderson, Farabow, Garrett & Dunner

[57] ABSTRACT

Hypocholesterolemically active RNA fractions having the following characteristics:
(a) Molecular weight by gel filtration: 11,000±9,000
(b) Base composition ratio of nucleic acid: uracil:-guanine:cytosine:adenine=1:1:2:1
(c) Infrared absorption spectrum: shown in FIG. 2
(d) Physiological characteristics: having a hypocholesterolemic activity in mammals.

These hypocholesterolemically active RNA fractions can be prepared by cultivating a microorganism belonging to the genus Streptococcus in an adequate culture medium therefor; and collecting the hypocholesterolemically active RNA fractions from the cultured cells of the microorganism. These hypocholesterolemically active RNA fractions can be used as an active ingredient of a hypocholesterolemic or antiatherosclerotic pharmaceutical composition together with a pharmaceutically acceptable carrier therefor to form a hypocholesterolemic or antiatherosclerotic pharmaceutical compositions, which is suitable for oral administration to mammals.

1 Claim, 2 Drawing Sheets

OTHER PUBLICATIONS

Rao et al., "Influence of Milk and Themophilus Milk on Plasma Cholesterol Levels and Hepatic Cholesterogenesis in Rats", J. of Food Sci., vol. 46, pp. 1339-1341 (1981).

Salvioli et al., "Bile Acid Transformation by the Intestinal Flora and Cholesterol Saturation in Bile", Digestion, vol. 23, pp. 80-88.

Hussain et al., "Activation of Lipolytic Activity of Streptococcus Cholesterogenesis in Rats", J. of Food Sci., vol. 46, pp. 1339-1344 (1981).

Rall et al., "Human Apolipoprotein E", J. Biol. Chem., vol. 275(8), pp. 4171-4178 (1982).

Slobodskaya et al., "Comparison of Hypocholesterolemic Effect . . . ", Biol. Abstract, 76(10) (1983).

Bergy's Manual of Determinative Bacteriology, 8th Ed., Williams and Williams, 1974.

Studies on Streptococci, I. Distribution of Fecal Streptococci in Main, Microbiol. Immuno.25(3), 257-269, 1981.

Studies on Streptococci, II., Colonization of Lactic Acid Bacteria Isolated from Rats and Humans in the Gastrointestinal Tract of Rats, Microbiol. Immunol. 26(5), 363-373, 1982.

Distribution and Colonization of Human Fecal Streptococci, The American J. of Clinical Nutrition 33, Nov. 1980, pp. 2458-2461.

Intestinal Enzyme Activities in Germfree, Conventional, and Gnotobiotic Rats Associated with Indigenous Microorganisms, Infection and Immunity, Mar. 1978, pp. 771-778.

Quantitative and Qualitative Altenation of Mucosal Alkaline Phosphatase by Indigenous Intestinal Microbes in the Upper Digestive Tract of the Rat, The American J. of Clinical Nutrition 32, Jan. 1979, pp. 187-188.

Intestinal Microflora and Aging: Age-Related Change of Lipid Metabolism in Germ-Free and Conventional Rates, Mechanisms of and Development, 16(1981), pp. 149-158.

Intestinal Microflora and Aging: Age-Related Change of Enzymes in the Liver and the Small Intestine of Germfree and Conventional Rates, Mechanisms of Ageing and Development, 17(1981), pp. 173-182.

HYPOCHOLESTEROLEMICALLY ACTIVE RNA FRACTIONS

BACKGROUND OF THE INVENTION

1. Field of the Invention

The present invention relates to novel hypocholesterolemically active ribonucleic acid (i.e, RNA) fractions, a process for preparing the same, a hypocholesterolemically active and/or anti-atherosclerotic pharmaceutical composition containing the same, and a method for reducing blood cholesterol in mammals.

2. Description of the Related Art

As is well-known in the art, several pharmaceutical preparations such as clofibrate and its related preparations have been proposed as therapeutical medicines for atherosclerosis or hyperlipidemia, considered to be a typical middle-aged or geriatric disease. However, the desired purposes are not fully satisfied by these known medicines from the viewpoint of, for example, pharmacological effects and side-effects, and there is a strong demand for the development of safer and more effective medicines.

SUMMARY OF THE INVENTION

Accordingly, an object of the present invention is to provide novel hypocholesterolemically active RNA fractions which can be safely administered to mammals.

Another object of the present invention is to provide a process for preparing novel hypocholesterolemically active RNA fractions capable of effectively reducing blood cholesterol in mammals.

A further object of the present invention is to provide a hypocholesterolemic or antiatherosclerotic pharmaceutical composition containing, as an active ingredient, novel RNA fractions.

A still further object of the present invention is to provide a method of reducing the blood cholesterol in mammals.

Other objects and advantages of the present invention will be apparent from the description set forth hereinbelow.

In accordance with the present invention, there is provided hypocholesterolemically active RNA fractions having the following characteristics:

(a) Molecular weight by gel filtration: 11,000±9,000

(b) Base composition ratio of nucleic acid: uracil:guanine:cytosine:adenine = 1:1:2:1

(c) Infrared absorption spectrum: shown in FIG. 2

(d) Physiological characteristics: having a hypocholesterolemic activity in mammals.

These hypocholesterolemically active RNA fractions can be prepared by cultivating a microorganism belonging to the genus Streptococcus in an adequate culture medium therefor; and collecting the hypocholesterolemically active RNA fractions from the cultured cells of the microorganism. The present hypocholesterolemically active RNA fractions can be used as an active ingredient of a hypocholesterolemic or antiatherosclerotic pharmaceutical composition together with a pharmaceutically acceptable carrier therefor to form a hypocholesterolemic or antiatherosclerotic pharmaceutical composition, which is suitable for oral administration to mammals.

BRIEF DESCRIPTION OF THE DRAWING

The present invention will be better understood from the description set forth below with reference to the accompanying drawings in which.

DESCRIPTION OF THE PREFERRED EMBODIMENTS

Figure 1:
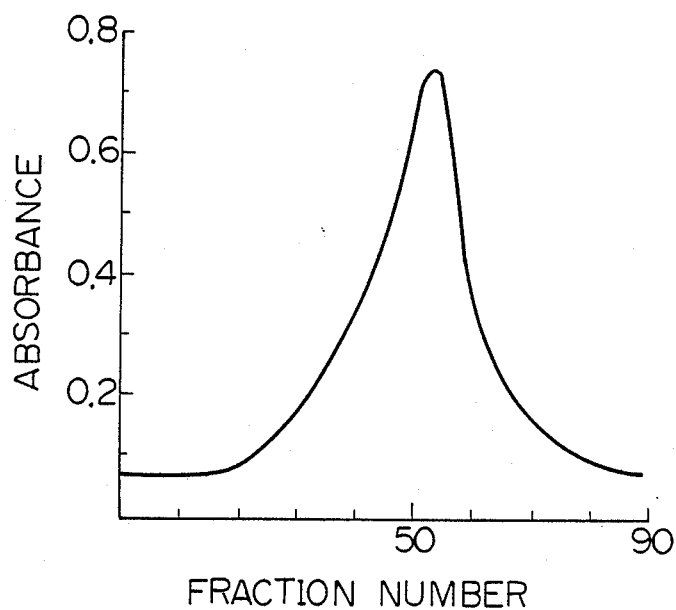
FIG. 1 illustrates the elution patterns of gel filtration of the hypocholesterolemically active RNA fractions of the present invention.

The present inventors have found that the novel RNA fractions obtained from microorganisms belonging to the genus Streptococcus can effectively reduce the blood cholesterol, and that constituents extracted from so-called gastrointestinal bacteria are substantially nontoxic when orally administered.

The microorganisms used in the preparation of the product, the manufacturing methods, the physiochemical characteristics, and the pharmacological effects of the hypocholesterolemically active RNA fractions according to the present invention will now be described in detail hereinbelow.

Microorganisms

1. Species

Microorganisms utilizable in the present invention belonging to the genus Streptococcus: such as Streptococcus faecium, Streptococcus faecalis, Streptococcus bovis, Streptococcus avium, Streptococcus durans, Streptococcus salivarius, Streptococcus mitis, Streptococcus equinus, and others are preferably shown.

Typical examples of such microorganisms have been deposited since July 15, 1982 in the Fermentation Research Institute (FRI) and transferred to FRI (i.e., International Depository Authority under Budapest Treaty in Japan). The deposition numbers are listed below in Table 1.

TABLE 1

| Strains | Deposition number |
| --- | --- |
| Streptococcus faecium | FERM BP-296 |
| Streptococcus faecalis | FERM BP-297 |
| Streptococcus avium | FERM BP-298 |
| Streptococcus salivarius | FERM BP-299 |
| Streptococcus durans | FERM BP-300 |
| Streptococcus mitis | FERM BP-301 |
| Streptococcus equinus | FERM BP-302 |

2. Microbiological Characteristics of Microorganisms

GENERAL MICROBIOLOGICAL CHARACTERISTICS

The microbiological characteristics of the microorganisms in the present invention are the same as those of known microorganisms belonging to the identical class. That is, the general microbiological characteristics, cultivation methods, and other properties correspond to those described in the following articles:

(1) Bergey's Manual of Determinative Bacteriology, 8th ed., 490–509 (1974)

(2) Int. J. Syst. Bact. 16, 114 (1966)

(3) Microbiol. Immunol. 25(3), 257–269 (1981)

(4) J. Clin. Pathol. 33, 53–57 (1980)

(5) J. General Microbiol. 128, 713–720 (1982)

(6) Applied Microbiol. 23 (6), 1131–1139 (1972)

Typical microbiological characteristics of the above-exemplified strains according to the present invention are summarized in Table 2.

TABLE 2

| Characteristics | Strains (FERM BP No.) | | | | | | |
|---|---|---|---|---|---|---|---|
| | 296 | 297 | 298 | 299 | 300 | 301 | 302 |
| Shape of cell | | | | spheroid | | | |
| Gram stain | + | + | + | + | + | + | + |
| Hemolysis | α | α | α | α | α | α | α |
| Growth at | | | | | | | |
| 10° C. | + | + | ± | − | + | − | − |
| 45° C. | + | + | + | ± | + | ± | + |
| 50° C. | + | − | − | − | + | − | − |
| Thermal resistance at 60° C. for 30 min | + | + | + | − | + | − | − |
| Growth in culture medium at pH 9.6 | + | + | + | − | + | − | − |
| Methylene blue reduction | + | + | − | − | + | − | − |
| Liquefaction of gelatin | − | − | − | − | − | − | − |
| Growth in culture medium containing NaCl (6.5%) | + | + | − | − | + | − | − |
| Growth in culture medium containing bile (40%) | + | + | + | − | + | − | + |
| Productivity of ammonia | + | + | ND*2 | − | + | ± | − |
| Hydrolysis of hippuric acid | − | ± | − | − | + | − | − |
| Growth in culture medium containing tellurite | − | + | − | ND*2 | − | ND*2 | − |
| Growth in culture medium containing TTC*1 | − | + | − | ND*2 | − | ND*2 | − |
| Acid production from | | | | | | | |
| Glucose | + | + | + | + | + | + | + |
| Esculin | ± | + | + | + | ± | ND*2 | + |
| Inulin | − | − | − | + | − | − | ± |
| Lactose | + | + | + | ± | + | ± | − |
| Glycerol | − | + | ± | − | − | − | − |
| Arabinose | + | − | + | − | − | − | − |
| Melezitose | − | + | ± | ND*2 | − | ND*2 | − |
| Sorbitol | − | + | + | − | − | − | − |
| Antigenic group | D | D | Q(D) | K | D | − | D |

*1 2,3,5-Triphenyltetrazolium chloride
*2 Not done

3. Cultivating Methods

These microorganisms can be cultivated in a conventional manner. For example, the bacterial cells can be collected by stationary cultivation in a Rogosa broth medium (Efthymiou, C., and Hansen, P. A. (1962). An antigenic analysis of *Lactobacillus acidophilus*. J. Infect. Dis. 110: 258–267) having the following composition, and can be harvested by centrifugation of the culture.

| Composition of Rogosa Broth Medium | |
|---|---|
| Trypticase | 10 g |
| Yeast extract | 5 g |
| Tryptose | 3 g |
| K$_2$HPO$_4$ | 3 g |
| KH$_2$PO$_4$ | 3 g |
| Triammonium citrate | 2 g |
| Tween 80 | 1 g |
| Glucose | 20 g |
| Cysteine hydrochloride | 0.2 g |
| Salt solution*1 | 5 ml |
| Distilled water | to 1 liter |

(pH 7, heat sterilization at 121° C. for 15 minutes)
*1 MgSO$_4$—7H$_2$O 11.5 g
FeSO$_4$—7H$_2$O 0.68 g
MnSO$_4$—2H$_2$O 2.4 g
Distilled water 100 ml

PREPARATION OF HYPOCHOLESTEROLEMICALLY ACTIVE RNA FRACTIONS

An example of typical procedures for the preparation of the hypocholesterolemically active RNA fractions according to the present invention is given as follows:

1. Collection of Microorganisms

Each of the microbial strains shown above is inoculated into a Rogosa broth medium and incubated without agitation at 37° C. for 5 to 15 hours, to yield a subsequent culture broth at a certain viable bacterial cell concentration. The culture broth is continuously centrifuged at 12,000 rpm, and the harvested bacterial cells are then washed 2 to 3 times in saline (0.85% NaCl).

2. Hot-Water Extraction

The washed cells are suspended in distilled water and heat-treated at 100° C. for 40 min, at 115° C. for 10 min, and at 115° C. for 30 min twice to be destructed and to be extracted simultaneously. The heat-treated cell suspension is centrifuged at 9,000 rpm for 10 min, and the supernatant is concentrated to form the desired extract.

3. Isolation of RNA Fractions (a) The above extract is dissolved in distilled water, added with a 10-fold volume of ethanol, and centrifuged at 12,000 rpm for 5 min or at 9,500 rpm for 10 min to separate the insoluble components in ethanol.

(b) The ethanol-insoluble components mentioned above are subjected to Dowex 50 W (Type H+) (The Dow Chemical Company, U.S.A.). The solvent is distilled water, and the components which have not adsorbed are incubated with cetyl pyridinium chloride solution (CPC solution) at 37° C. for 3 hrs. The resultant materials are then centrifuged at 12,000 rpm for 5 min or at 9,500 rpm for 10 min. The precipitation is dissolved into a 2M NaCl solution, added with a 5 to 6-fold volume of ethanol and centrifuged (at 12,000 rpm for 5 min). The precipitation by ethanol is again treated with Dowex 50 W to obtain the fractions.

4. Purification

The fractions mentoned above are treated with deoxyribonucleases. After the enzyme is removed by a phenol-treatment followed by dialysis, the fractions are purified by Sephadex G-75 (Pharmacia Fine Chemicals) column chromatography to obtain the desired active RNA fractions.

In general, these hypocholesterolemically active RNA fractions can be prepared according to its physiochemical characteristics, mentioned below, by many of the isolation and purification procedures already widely employed in the field concerned, such as precipitation-dissolution and extraction, solvent extraction, dialysis, column chromatography, electrophoresis, gel filtration, or any combination of these procedures. Therefore, the present invention is by no means limited to a specified procedure.

That is, the preparation of the present invention is related to the preparation methods of hypocholesterolemically active products, which are composed of RNA fractions and obtained from microorganisms belonging to the genus Streptococcus, because the pharmacological activity is found in the RNA fractions.

PHYSICOCHEMICAL CHARACTERISTICS OF HYPOCHOLESTEROLEMICALLY ACTIVE RNA FRACTIONS

The physiochemical and physiological characteristics of the hypocholesterolemically active RNA fractions of the present invention are as follows.

1. Chemical Nature, Solubility And Thermal Properties

The powdered sample obtained by lyophilization of the RNA fractions is light brown or yellowish brown and is soluble in water and 1N NaOH solution but insoluble in organic solvents such as alcohol, ether and benzene. By heating, the powder turns brown at about 200° C. and dark brown at 220° C.

2. Molecular Weight (i) Sephadex Column Chromatography

A single peak is given by gel filtration using a Sephadex G-75 column (2.5×47 cm, Pharmacia Fine Chemical) eluted with a 0.2M pyridine-acetic acid buffer (pH 5.0) as a solvent. The result is shown in FIG. 1, where the ordinate and abscissa show the O.D. at 480 nm in phenol-$H_2SO_4$ method and the fraction number, respectively.

(ii) Polyacrylamide Gel Electrophoresis

A 400 μg amount of the sample was electrophoresed in a buffer containing 0.04M Tris (hydroxymethyl) aminomethane, 0.02M sodium acetate, 0.002M ethylenediaminetetraacetic acid, and 0.02% sodium dodecyl sulfate (pH 7.5), at 30 mA for 6 hrs. The sample moved longer than a standard RNA of E. coli or almost the same as bromophenol blue does on 10% or 12% polyacrylamide gels, respectively, and moved between bromphenol blue and xylene cyanol on the 20% gels.

The molecular weight of the sample was thus estimated by these findings to be 11,000±9,000.

3. Infrared Absorption Spectrum

Figure 2:
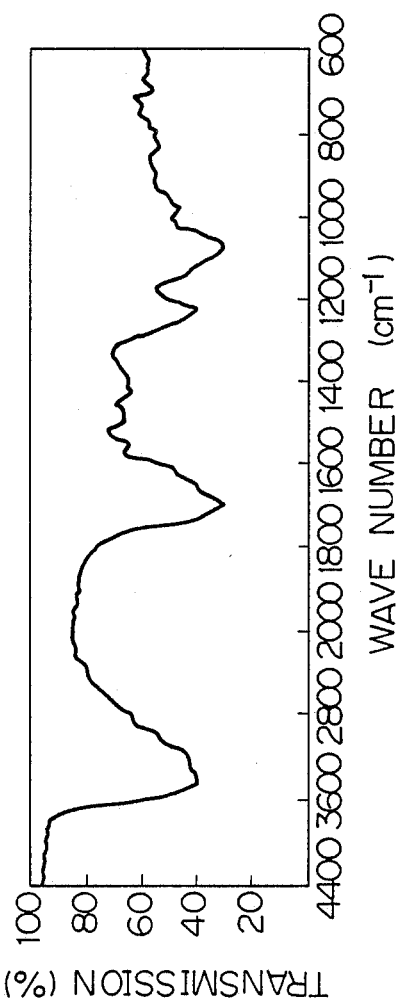
FIG. 2 illustrates an infrared absorption spectrum profile of the hypocholesterolemically active RNA fractions of the present invention.

The infrared absorption spectrum of the hypocholesterolemically active RNA fractions, measured by an infrared spectrometer (model JASCO A-302, Japan Spectroscopic Co., Ltd.) is shown in FIG. 2, where the abscissa and ordinate show the wave number and percent transmission, respectively.

4. Base Composition of Nucleic Acid

The base composition of the nucleic acid, which was decomposed with 6N HCl at 100° C. for 3 hrs, was estimated at U(uracil):G(guanine):C(cytosine):A(adenine)=1:1:2:1 by high speed liquid chromatography (Patisil-10 scx column (Gasukuro Kogyo Inc.), wherein the solvent was a 0.05M $KH_2PO_4$ buffer (pH 3.05), the flow rate was 1 ml/min, and the wavelength was 260 nm).

5. Physiological Characteristics

The hypocholesterolemically active RNA fractions have an activity which will reduce the blood cholesterol level in mammals, when administered orally.

Pharmacological Actions

1. As shown in each example hereinbelow, the present antiatherosclerotic drug composed of the hypocholesterolemically active RNA fractions of the present invention is extremely effective in reducing the blood cholesterol level in mammals. Accordingly, this drug is useful as a therapeutica or preventive medicine for diseases closely related to atherosclerosis, hyperlipidemia, cerebral atherosclerosis, hyperlipoproteinemia, xanthomatosis, cholecystolithiasis, heptao-cholepathia, nephropathy (nephrosis syndrome), hypertension, diabetes, cardiopathia, endocrinism, hypothyreosis, adiposis, and others.

The preparation of the present invention can be administered to mammals via oral, intraperitoneal, and intravenous, and other administration routes. The amount per dosage is preferably about 1 μg to 0.5 g/kg body weight. An oral administration of about 0.1 mg to 50 mg/kg body weight is preferred. Any drug form of the present invention can be chosen and used as a solution in physiological saline and others, injections, lyophilized powder, etc., suppository, entericcoated tablets, sublingual tablets, granules, tablets, capsules, etc., with appropriate carriers, diluent bases, diluents, etc.

2. Acute Toxicity

As shown in the examples hereinbelow, an $LD_{50}$ of the hypocholesterolemically active RNA fractions according to the present invention is more than 1,370 mg/kg body weight, intraperitoneally in mice. The substance is substantially nontoxic upon oral administration.

Examples

The present invention will now be further shown by, but is by no means limited to, the following examples.

Example 1

Preparation and purification of the hypocholesterolemically active RNA fractions.

Preparation and Purification of RNA Fractions

A 64 liter amount of Rogosa broth medium inoculated with Streptococcus avium AD 2003 (FERM BP-298) was incubated at 37° C. for 12 hrs without agitation. The obtained 207 g of wet bacterial cells were completely agitated with 2 liters of distilled water and were heat-treated at 100° C. (under atmospheric condition) for 40 min, at 115° C. for 10 min, and at 115° C. for 30 min (twice). The heat treated cell suspension was separated into supernatant and precipitation fractions by centrifugation at 9,000 rpm for 10 min and the supernatant was concentrated to obtain an extract I (yield was 36.7% by weight).

The obtained extract I was dissolved in 30 ml of distilled water, added with 300 ml of ethanol with agitation, and centrifuged at 9,500 rpm for 10 min) to separate the supernatant (i.e., ethanol-soluble) and precipitation (ethanol-insoluble) fractions. The resultant precipitation fraction was again subjected to the same procedure.

The ethanol-insoluble fraction was dissolved in 700 ml of distilled water, and was added into 1,000 ml of ion-exchange resin Dowex 50 W (Type H+) (The Dow Chemical Company, U.S.A.), with agitation. The solvent was removed by decantation. The ion-exchange resin was then washed 6 times with 1,000 ml of distilled water to remove unadsorbed materials.

The obtained solution containing the unadsorbed materials was concentrated, dissolved in 1,200 ml of distilled water, and incubated at 37° C. for 3 hrs with 180 ml of a 10% cetyl pyridium chloride (CPC) solution (Nakarai Chemicals, Ltd.).

The precipitation obtained by centrifugation at 9,500 rpm for 10 min after the 3 hr-incubation was dissolved in 90 ml of a 2M NACl solution, added with 540 ml of ethanol with agitation, and centrifuged at 12,000 rpm for 5 min to obtain the precipitation.

The above-mentioned process was repeated 4 times and the obtained precipitation material was treated with the same method as above with 1,000 ml of Dowex 50 W (Type H+) (The Dow Chemical Company, U.S.A.) to obtain CPC free fraction II (yield was 8.7% by weight).

A 300 mg amount of the fraction II obtained above was added with 30 ml of a DNase (Sigma Chemical Company, Deoxyribonuclease I) solution (containing 1 ml solution composed of 0.1M Tris-acetic acid buffer (pH 8.0)+20 mM $MgSO_4$+25 mM $CaCl_2$, and 1 mg DNase) which was treated with bentonite and incubated at 37° C. for 24 hrs.

After the enzyme-treatment, 30 ml of water saturated with phenol was added to the incubated sample, mixed completely, centrifuged at 12,000 rpm for 5 min, the water layer was isolated.

To the remaining phenol layer, 30 ml of phenol-saturated water was added and the same process was carried out 3 times.

Thus, the water layer obtained was dialysed and concentrated to obtain the enzyme-treated material.

The enzyme-treated material was purified by gel filtration with Sephadex G-75 column (Pharmacia Fine Chemicals) (solvent was 0.2M pyridineacetic acid buffer, pH 5.0) to obtain the desired RNA fractions (yield was 2.5% by weight).

Table 3 shows the yield of Extract I and other fractions in each preparation process.

TABLE 3

| | yield (%) | RNA (%) | DNA (%) | sugar (%) | protein (%) |
|---|---|---|---|---|---|
| Extract I | 36.7 | | 42.8 | 16.2 | 14.9 |
| Fraction II | 8.7 | 106.2 | 8.8 | trace | 3.8 |
| RNA fractions | 2.5 | 108.6 | trace | trace | 2.9 |

In Table 3, RNA was determined by the orcinol method (the standard sample was yeast RNA), DNA by the diphenylamine method (the standard was calf thymus DNA), sugar of Extract I by the phenol-$H_2SO_4$ method, sugar of the other fractions by the anthron method (the standard was glucose), and protein by the Lowry method (the standard was bovine serum albumin).

On the other hand, it was assured that the same RNA fractions were obtained as in Example 1 from the other strains shown in Table 1.

The physiochemical characteristics of the RNA fractions were as shown above.

Example 2

Pharmacological effect of the hypocholesterolemically active RNA fractions

1. Hypocholesterolemic Activity (I)

Solutions containing the equivalent amount of 25 mg/kg body weight per ml of the lyophilized hypocholesterolemically active RNA fractions were prepared. These samples were orally administered (1 ml/day/rat) to conventional rats (18 week-old, male, average body weight 240 g, 5 rats per group) and conventional and germfree mice (10 week-old, male, average body weight 20.1 g, 5 mice per group). The rats and mice were bred for 8 to 12 weeks. Arterial blood was then collected from the abdominal aorta of these animals and serum samples were separated by centrifugation from the whole blood. The cholesterol level was determined by using Choleskit (Kanto Chemical Co., Inc., Zurkowski method).

The results are summarized in Table 4. The values listed in the table are a reduction rate (%) from the values in the control groups to which no sample is dosed. The composition (% by weight) of the diet, given ad libitum, is shown in Table 5.

TABLE 4

| Animals | Reduction rate (%) |
|---|---|
| Conventional rats (12 weeks) | 20.3 ± 0.6 |
| Conventional mice (8 weeks) | 30.7 ± 1.1 |
| Germfree mice (8 weeks) | 20.0 ± 0.8 |

TABLE 5

| Composition | Weight (%) |
|---|---|
| Milk casein | 20 |
| Soybean oil | 10 |
| Wheat starch | 61 |
| Minerals*[1] | 4 |
| Vitamin mixture*[2] | 2 |
| Powdered filter paper (cellulose) | 3 |

*[1]Phillips-Hart salt* (Iwai Kagaku Co., Ltd.)
| | |
|---|---|
| $K_2HPO_4$ | 322 (g/1,000 g) |
| $CaCO_3$ | 300 |
| NaCl | 167 |
| $MgSO_4$ | 102 |
| $Ca_2P_2O_7$ | 75 |
| Ferric citrate | 27.5 |
| $CuSO_4.5H_2O$ | 0.3 |
| $ZnCl_2$ | 0.25 |
| $MnSO_4.4H_2O$ | 5.1 |
| KI | 0.8 |
| $CoCl_2.6H_2O$ | 0.05 |

*Phillips, P. H. and Hart, E. B., The effect of organic dietary constituents upon chronic fluorine toxicosis in the rat, J. Biol. Chem., 109, 657, (1935).

*[2]Panvitan powder (Takeda Chemical Industries, Ltd.)
| | |
|---|---|
| | 20 (g/100 g) |
| Choline chloride | 10 Calcium |
| pantothenate | 0.15 |
| Pyridoxine hydrochloride | 0.006 |
| Inositol | 1.0 |
| Wheat starch | 68.8 |

2. Hypocholesterolemic activity (II)

The above-mentioned samples were orally administered (1 ml/day)rat) to conventional rats (18 week-old, male, average body weight 238 g, 5 rats per group) and conventional and germfree mice (10 week-old, male, average body weight 22 g, 5 mice per group) for 12 weeks. The blood cholesterol level was determined as mentioned above. The results are shown in Table 6.

The terms cholesterol-loaded and frustose-loaded in the table mean the addition of 1% cholesterol into the above-mentioned diet and the substitution of fructose for the total amount of wheat starch in the above-mentioned diet, respectively. The values in the table are the reduction rate (%) from the values of the no dosage control group.

TABLE 6

| Animals | Reduction rate (%) |
|---|---|
| Germfree mice[*1] | 33.1 ± 1.0 |
| Conventional mice[*1] | 37.2 ± 0.5 |
| Conventional rats[*1] | 48.1 ± 1.0 |
| Conventional rats[*2] | 39.7 ± 1.1 |

[*1]Cholesterol-loaded diet
[*2]Fructose-loaded diet

3. Hypocholesterolemic Activity (III)

Solution containing the equivalent amount of 11.3 mg/kg body weight per ml of the RNA fractions were orally administered (0.5 ml/day/rat) for 2 weeks to hyperlipidemic rats (8 week-old, male, average body weight 222 g, 5 rats per group) fed a cholesterol-loaded diet. The blood cholesterol level was determined as mentioned above. The results are shown in Table 7. The value of the administration group is the cholesterol reduction rate (%) to the no dosage control group.

TABLE 7

| Animals | Reduction rate (%) |
|---|---|
| Administered | 41.2 |
| Control | 0 |

4. Dose Response

Solutions containing 0.1 mg–20 mg/ml of the hypocholesterolemically active RNA fractions were orally administered (1 ml/day/rat) to conventional rats (6 week-old, male, average body weight 210 g, 5 rats per group) for 4 weeks. The blood cholesterol level was determined as mentioned above (control group was no dosed group). The results are shown in Table 8.

TABLE 8

| Dosage (mg/rat) | Reduction rate (%) |
|---|---|
| Control | 0 |
| 0.1 | 7.4 ± 0.6 |
| 1 | 12.5 ± 1.0 |
| 10 | 43.3 ± 0.9 |

TABLE 8-continued

| Dosage (mg/rat) | Reduction rate (%) |
|---|---|
| 20 | 48.2 ± 0.8 |

5. Acute Toxicity

Physiological saline samples (0.5 ml/mouse) containing 1, 10, and 100 mg of the hypocholesterolemically active RNA fractions were intraperitoneally administered to ICR mice (6 week-old male, average body weight 31.6±0.6 g, 10 mice per group). The thanatobiologic observation of mice was carried out for 14 days. The control material was physiological saline.

The $LD_{50}$ value was calculated according to the Behrens-Kärber method was more than 1,370 mg/kg body weight. The substance was substantially nontoxic on oral administration.

6. Pharmaceutical preparations (1) A 25 mg amount of the purified hypocholesterolemically active RNA fractions was uniformly mixed with 275 mg of purified starch powder, and the tablets for oral administration were then formed. Each tablet corresponded to a dosage of $3 \times 10^{10}$ heat-treated cells/kg body weight for an adult having a body weight of 50 kg.

(2) The hypocholesterolemically active RNA fractions were uniformly mixed with diluent bases such as calcium carbonate, lactose, etc., lubricants such as stearic acid, talcium, etc., and other additives, and the tablets then can be formed for oral administration. The daily dosage of the hypocholesterolemically active RNA fractions is usually 0.1 mg–50 mg/kg body weight.

(3) The hypocholesterolemically active RNA fractions (900 mg) were suspended and dissolved in distilled water (30 ml) sweetened with syrup, and syrups were then formed.

We claim:

1. Hypocholesterolemically active RNA fractions derived from a microorganism selected from the group consisting of Streptococcus faecium FERM BP-296, Streptococcus faecalis FERM BP-297, Streptococcus avium FERM BP-298, Streptococcus salivarius FERM BP-299, Streptococcus durans FERM BP-300, Streptococcus mitis FERM BP-301, and Streptococcus equinus FERM BP-302, and having the following characteristics:

(a) Molecular weight by gel filtration: 11,000±9,000;
(b) Base composition ratio of nucleic acid:uracil:-quanine:cytosine:adenine=1:1:2:1;
(c) Infrared absorption spectrum: shown in FIG. 2; and
(d) Physiological characteristics: having a hypocholesterolemic activity in mammals.

* * * * *

UNITED STATES PATENT AND TRADEMARK OFFICE
CERTIFICATE OF CORRECTION

PATENT NO. : 4,824,945
DATED : April 25, 1989
INVENTOR(S) : Yasuo Kawai et al

It is certified that error appears in the above-identified patent and that said Letters Patent is hereby corrected as shown below:

On the title page assignee should read

--Assignee: Kabushiki Kaisya Advance Kaihatsu Kenkyujo
            Nihonbashi, Japan --.

In the Abstract of the Disclosure, line 11, delete "Streptococcus" and insert --Streptococcus--; line 20, delete "compositions" and insert --composition--.

Signed and Sealed this

Twenty-first Day of November, 1989

Attest:

JEFFREY M. SAMUELS

Attesting Officer         Acting Commissioner of Patents and Trademarks